(12) United States Patent
Chen et al.

(10) Patent No.: US 10,399,851 B2
(45) Date of Patent: Sep. 3, 2019

(54) ELECTRICALLY CONDUCTIVE PATTERNS WITH WIDE LINE-WIDTH AND METHODS FOR PRODUCING SAME

(71) Applicant: 3M INNOVATIVE PROPERTIES COMPANY, St. Paul, MN (US)

(72) Inventors: Chi-fan Chen, Taichung (TW); Wan-chun Chen, Zhubei (TW); Yu-chih Lin, Taoyuan (TW); Tze Yuan Wang, New Taipei (TW); Chia-yuan Liu, Yangmei (TW)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/515,399

(22) PCT Filed: Sep. 28, 2015

(86) PCT No.: PCT/US2015/052627
§ 371 (c)(1),
(2) Date: Mar. 29, 2017

(87) PCT Pub. No.: WO2016/053866
PCT Pub. Date: Apr. 7, 2016

(65) Prior Publication Data
US 2017/0217768 A1 Aug. 3, 2017

Related U.S. Application Data

(60) Provisional application No. 62/057,546, filed on Sep. 30, 2014.

(51) Int. Cl.
*B81C 1/00* (2006.01)
*A61B 5/145* (2006.01)
*H05K 3/06* (2006.01)
*B41M 1/26* (2006.01)

(52) U.S. Cl.
CPC ...... *B81C 1/00388* (2013.01); *A61B 5/14532* (2013.01); *B41M 1/26* (2013.01);
(Continued)

(58) Field of Classification Search
None
See application file for complete search history.

(56) References Cited

U.S. PATENT DOCUMENTS 3,538,847 A 11/1970 Heilman
5,122,442 A * 6/1992 Moskowitz ............... G03F 7/12
430/157

(Continued)

FOREIGN PATENT DOCUMENTS

CN 101246175 8/2008
CN 101303357 11/2008
(Continued)

OTHER PUBLICATIONS

Libioulle, "Contact-Inking Stamps for Microcontact Printing of Alkanethiols on Gold", Langmuir, American Chemical Society, 1999, vol. 15, No. 02, pp. 300-304.
(Continued)

*Primary Examiner* — Jiong-Ping Lu
(74) *Attorney, Agent, or Firm* — Yufeng Dong

(57) ABSTRACT

A master tool is provided with an ink pattern on a major surface thereof. The ink pattern is formed by a screen printing process. A stamp-making material is applied to the major surface of the master tool to form a stamp having a stamping pattern being negative to the ink pattern of the master tool. The stamping pattern is inked with an ink composition and contacted with a metalized surface to form a printed pattern on a metalized surface of a substrate according to the stamping pattern. Using the printed pattern
(Continued)

as an etching mask, the metalized surface is etched to form electrically conductive traces on the substrate.

19 Claims, 6 Drawing Sheets

(51) Int. Cl.
> B41M 1/12 (2006.01)
> B41C 1/00 (2006.01)
> A61B 5/15 (2006.01)
> H05K 1/03 (2006.01)
> H01L 21/48 (2006.01)

(52) U.S. Cl.
CPC ............ *B81C 1/00* (2013.01); *B81C 1/00206* (2013.01); *B81C 1/00396* (2013.01); *H05K 3/061* (2013.01); *A61B 5/150022* (2013.01); *A61B 5/150274* (2013.01); *A61B 5/150358* (2013.01); *A61B 2562/0295* (2013.01); *A61B 2562/125* (2013.01); *B01J 2219/00382* (2013.01); *B41C 1/003* (2013.01); *B41M 1/12* (2013.01); *B81C 2201/01* (2013.01); *H01L 21/4867* (2013.01); *H05K 1/0393* (2013.01); *H05K 2203/0108* (2013.01); *H05K 2203/1545* (2013.01)

(56) References Cited

U.S. PATENT DOCUMENTS

| | | | |
|---|---|---|---|
| 5,512,131 | A | 4/1996 | Kumar |
| 5,708,247 | A | 1/1998 | McAleer et al. |
| 6,020,047 | A | 2/2000 | Everhart |
| 6,048,623 | A | 4/2000 | Everhart |
| 6,821,462 | B2 | 11/2004 | Schulman |
| 2003/0124757 | A1* | 7/2003 | Lee .................. B82Y 10/00 438/48 |
| 2005/0008675 | A1 | 1/2005 | Bhatia |
| 2006/0174789 | A1 | 8/2006 | Liebau et al. |
| 2008/0000373 | A1 | 1/2008 | Petrucci-Samija et al. |
| 2008/0020452 | A1 | 1/2008 | Popovich et al. |
| 2009/0218310 | A1* | 9/2009 | Zu .................. B82Y 10/00 216/11 |
| 2010/0258968 | A1 | 10/2010 | Zu |
| 2012/0177769 | A1 | 7/2012 | Wagner et al. |

FOREIGN PATENT DOCUMENTS

| | | |
|---|---|---|
| IN | 222754 | 8/2008 |
| IN | 226902 | 1/2009 |
| JP | 05042511 | 2/1993 |
| JP | 07090558 | 4/1995 |
| KR | 1020060132380 | 12/2006 |

OTHER PUBLICATIONS

Love, "Self-Assembled Monolayers of Thiolates on Metals as a Form of Nanotechnology", Chemical Reviews, 2005, vol. 105, No. 04, pp. 1103-1169.

Ulman, "Formation and Structure of Self-Assembled Monolayers", Chemical Reviews, 1996, vol. 96, No. 04, pp. 1533-1554.

International Search Report for PCT International Application No. PCT/US2015/052627, dated Jan. 22, 2016, 4 pages.

* cited by examiner

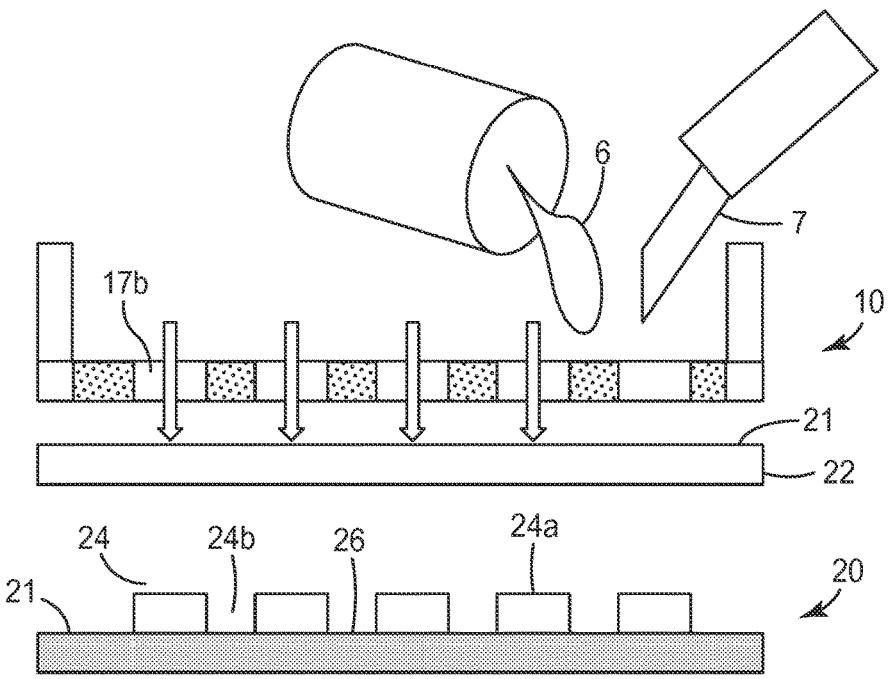
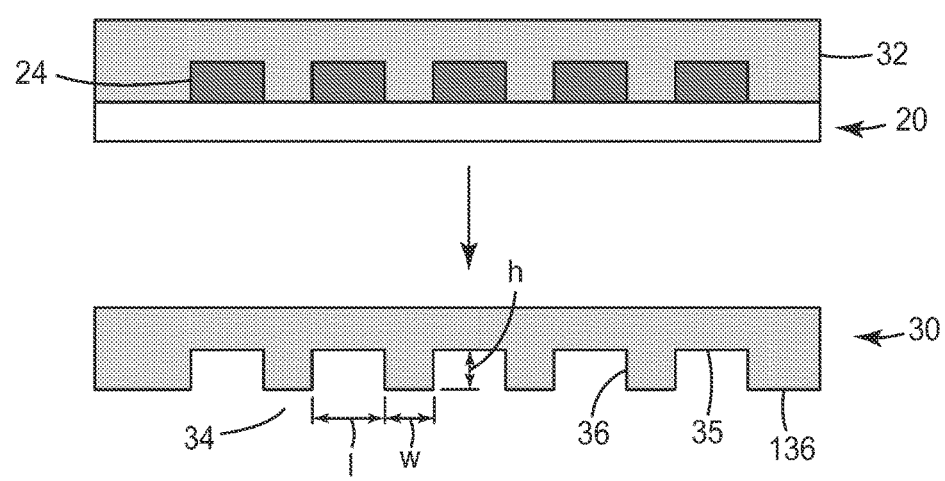
FIG. 5

ELECTRICALLY CONDUCTIVE PATTERNS WITH WIDE LINE-WIDTH AND METHODS FOR PRODUCING SAME

CROSS REFERENCE TO RELATED APPLICATIONS

This application is a national stage filing under 35 U.S.C. 371 of PCT/US2015/052627, filed Sep. 28, 2015, which claims the benefit of U.S. Application No. 62/057,546, filed Sep. 30, 2014, the disclosure of which is incorporated by reference in its/their entirety herein.

TECHNICAL FIELD

The present disclosure relates to articles having electrically conductive patterns with a wide line-width and methods of forming the same.

BACKGROUND

Conventional screen printing processes have been used to prepare metallic patterns on a substrate where an electrically conductive paste is directly printed onto the substrate surface through a printing plate to form the metallic patterns.

Microcontact printing has been used to generate patterns of functionalizing molecules on a surface of a substrate to form a patterned self-assembled monolayer (SAM). See, for example, U.S. Pat. No. 5,512,131 (Kumar et al.)

SUMMARY

While films with electrically conductive patterns made by the conventional screen printing process can include metallic traces with a wide line width (e.g., 100 micrometers or greater), the quality of the metallic traces is unstable and has certain technology limits on the performance. Thus, there is a desire to improve the mass-productivity and quality of electrically conductive traces with a wide line-width (e.g., 30 micrometers or more).

Some embodiments described herein provide master tools that can be prepared by a screen printing process. Some master tools described herein can provide pattern elements having a relief height of at least 10 micrometers, and a lateral dimension of at least 30 micrometers. It is technically difficult, time-consuming, and expensive to prepare photoresist patterns by conventional photolithography techniques (e.g., the photoresist pattern on silicon in U.S. Pat. No. 5,512,131) to obtain such high relief heights and such wide lateral dimensions as achieved in this disclosure.

Briefly, in one aspect, the present disclosure describes methods of forming an electrically conductive pattern on a substrate. A master tool can be provided with an ink pattern on a major surface thereof. The ink pattern can be formed by a screen printing process. A stamp-making material can be applied onto the ink pattern of the master tool to form a stamp having a stamping pattern being negative to the ink pattern. A stamping surface of the stamping pattern can be inked with an ink composition and contacted with a metalized surface to form a printed pattern thereon according to the stamping pattern. Using the printed pattern as an etching mask, the metalized surface is etched to form electrically conductive traces.

In one embodiment, a method includes screen-printing an ink pattern onto a major surface of a master tool. The ink pattern includes a plurality of ink pattern elements extending away from the major surface and one or more indentations formed between the respective ink pattern elements that are adjacent to each other. A stamp-making material is applied to the major surface of the master tool to form an elastomeric stamp having a stamping pattern. The stamping pattern is negative to the ink pattern of the master tool. The stamping pattern includes a base surface and one or more stamping pattern elements extending away from the base surface. The stamping pattern elements correspond to the indentations of the master tool, and each of the stamping pattern elements has a stamping surface.

In another embodiment, a method of forming an electrically conductive pattern on a substrate is provided. The method includes providing a master tool having an ink pattern on a major surface of a master substrate thereof. The ink pattern includes a plurality of ink pattern elements extending away from the major surface and one or more indentations formed between the respective ink pattern elements that are adjacent to each other. A stamp-making material is applied to the major surface of the master tool to form an elastomeric stamp having a stamping pattern. The stamping pattern is negative to the ink pattern of the master tool. The stamping pattern includes a base surface and one or more stamping pattern elements extending away from the base surface. The stamping pattern elements correspond to the indentations of the master tool, and each of the stamping pattern elements has a stamping surface. The method further includes inking the stamping surfaces of the stamp with an ink composition. The stamping surfaces of the stamp are contacted with the metalized surface of the substrate to transfer the ink composition from the stamping surfaces of the stamp to the metalized surface and create a printed pattern thereon. The method further includes etching, using the printed pattern as an etching mask, the metalized surface to form one or more electrically conductive traces on the substrate.

Various unexpected results and advantages are obtained in exemplary embodiments of the disclosure. One such advantage of exemplary embodiments of the present disclosure is that some master tools described herein can provide pattern elements having a relief height of at least 10 micrometers, and a lateral dimension of at least 30 micrometers. It is technically difficult, time-consuming, and expensive to prepare photoresist patterns by conventional photolithography techniques to obtain such high relief heights and such wide lateral dimensions as achieved in this disclosure.

Listing of Exemplary Embodiments

Exemplary embodiments are listed below. It is to be understood that any of embodiments A to N and embodiments O to AA can be combined.

Embodiment A

A method comprising:

screen-printing an ink pattern onto a major surface of a master tool, the ink pattern comprising a plurality of ink pattern elements extending away from the major surface and one or more indentations formed between the respective ink pattern elements that are adjacent to each other; and applying a stamp-making material to the major surface of the master tool to form an elastomeric stamp having a stamping pattern, the stamping pattern being negative to the ink pattern of the master tool, the stamping pattern comprising a base surface and one or more stamping pattern elements extending away from the base surface, the stamping pattern elements corresponding to the indentations of the master tool, and each of the stamping pattern elements having a stamping surface.

Embodiment B

The method of embodiment A, wherein at least one of the ink pattern elements has a relief height of at least 10 micrometers.

Embodiment C

The method of any preceding embodiment, wherein at least one of the ink pattern elements has a lateral dimension of at least 30 micrometers.

Embodiment D

The method of any preceding embodiment, wherein at least one of the ink pattern elements has a draft angle of 0 to 10 degrees.

Embodiment E

The method of any preceding embodiment, wherein at least one of the indentations of the master tool has a lateral dimension of at least 30 micrometers.

Embodiment F

The method of any preceding embodiment, wherein screen-printing the ink pattern further comprises providing a screen having a screen pattern thereon, the screen pattern comprising open areas configured to allow fluid to pass through the screen, positioning the screen adjacent to the major surface of the master tool, and applying ink to pass through the open areas of the screen to form an ink pattern on the major surface of the master tool.

Embodiment G

The method of embodiment F, wherein providing the screen comprises providing a photosensitive emulsion layer on the screen, and exposing the photosensitive emulsion layer via a photomask to develop the screen pattern thereon.

Embodiment H

The method of embodiment G, wherein the photosensitive emulsion layer comprises a photosensitive material including polyvinylacetate, poly vinyl alcohol, acrylate monomer, or a combination thereof.

Embodiment I

The method of any preceding embodiment, wherein the stamp-making material includes uncured polydimethylsiloxane (PDMS).

Embodiment J

The method of any preceding embodiment, wherein the master tool comprises a glass substrate.

Embodiment K

The method of any preceding embodiment, wherein at least one of the stamping surfaces has a lateral dimension of at least 30 micrometers.

Embodiment L

The method of any preceding embodiment, wherein at least one of the stamping pattern elements has a characteristic height of at least 10 micrometers.

Embodiment M

The method of any preceding embodiment, wherein at least one of the stamping surfaces has a lateral dimension of at least 30 micrometers.

Embodiment N

An elastomeric stamp, produced by the method of any preceding embodiment.

Embodiment O

A method of forming an electrically conductive pattern on a substrate, comprising:
providing a master tool having an ink pattern on a major surface of a master substrate thereof, the ink pattern comprising a plurality of ink pattern elements extending away from the major surface and one or more indentations formed between the respective ink pattern elements that are adjacent to each other;
applying a stamp-making material to the major surface of the master tool to form an elastomeric stamp having a stamping pattern, the stamping pattern being negative to the ink pattern of the master tool, the stamping pattern comprising a base surface and one or more stamping pattern elements extending away from the base surface, the stamping pattern elements corresponding to the indentations of the master tool, and each of the stamping pattern elements having a stamping surface;
inking the stamping surfaces of the stamp with an ink composition;
contacting the stamping surfaces of the stamp with the metalized surface of the substrate to transfer the ink composition from the stamping surfaces of the stamp to the metalized surface and create a printed pattern thereon; and
etching, using the printed pattern as an etching mask, the metalized surface to form one or more electrically conductive traces on the substrate.

Embodiment P

The method of embodiment O, wherein providing the master tool further comprises providing a screen having a screen pattern with open areas thereon, applying ink to pass through the open areas of the screen to form the ink pattern on the major surface of a master substrate, and drying the ink pattern to form the master tool.

Embodiment Q

The method of embodiment O or P, wherein at least one of the stamping pattern elements has a characteristic height of at least 10 micrometers.

Embodiment R

The method of any one of embodiments O to Q, wherein at least one of the stamping surfaces has a lateral dimension of at least 30 micrometers.

Embodiment S

The method of any one of embodiments O to R, wherein at least one of the electrically conductive traces has a lateral dimension of at least 30 micrometers.

Embodiment T

The method of any one of embodiments O to S, wherein the master tool comprises a glass substrate.

Embodiment U

The method of any one of embodiments O to T, wherein the stamp-making material includes uncured polydimethylsiloxane (PDMS).

Embodiment V

The method of any one of embodiments O to U, wherein the ink composition comprises a functionalizing molecule, wherein the functionalizing molecule comprises a functional group capable of binding to the metalized surface of the substrate.

Embodiment W

The method of any one of embodiments O to V, wherein the substrate includes a polymeric film and a metal layer disposed on the polymeric film.

Embodiment X

The method of embodiment W, wherein the polymeric film comprises poly(ethylene terephthalate) (PET), poly (butylenes terephthalate) (PBT), poly(ethylerne naphthalate) (PEN), or a combination thereof.

Embodiment Y

The method of embodiment W or X, wherein the metal layer includes at least one of copper, silver, aluminum, gold, and combinations thereof.

Embodiment Z

An electrically conductive pattern on a substrate, formed by the method of any one of embodiments O to Y.

Embodiment AA

A glucose test strip comprising the electrically conductive pattern of embodiment Z.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which:

FIG. 4 is a schematic illustration of forming a master tool, according to one embodiment.

FIG. 5 is a schematic illustration of forming a stamp, according to one embodiment.

Figure 1:
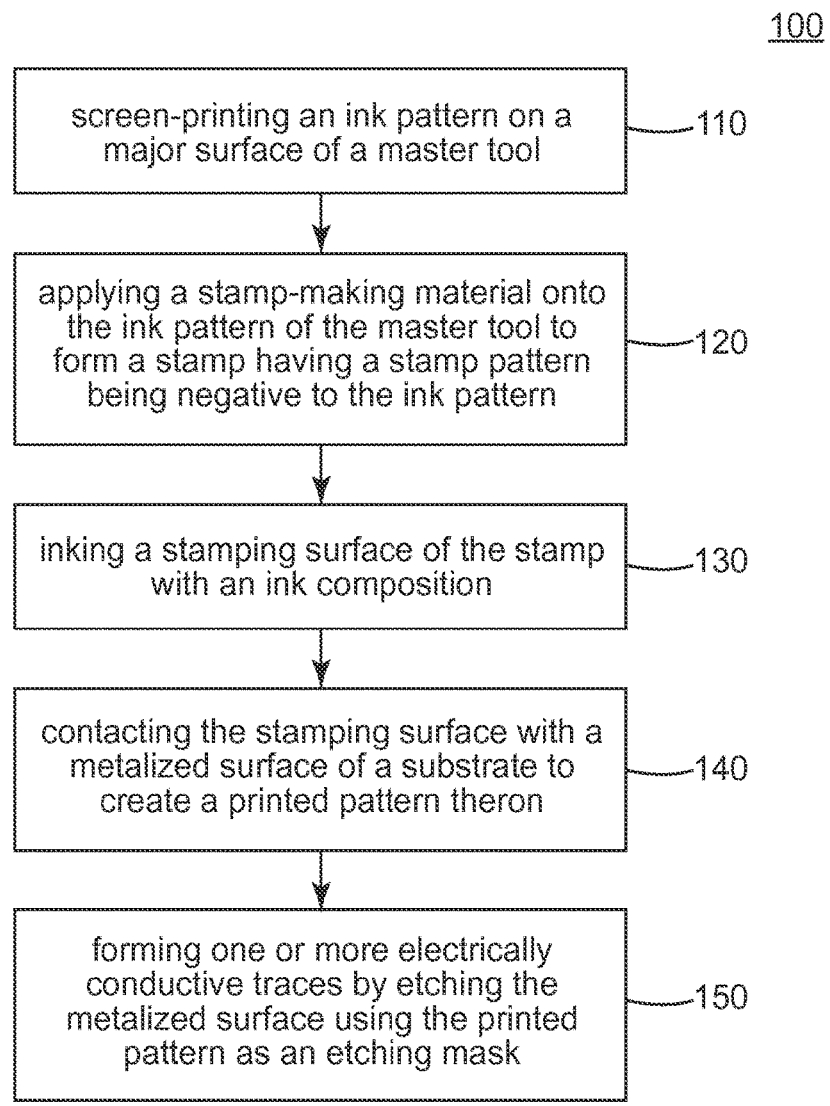
FIG. 1 is a flow diagram illustrating a method of forming an electrically conductive pattern on a substrate, according to one embodiment.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure describes electrically conductive patterns with a wide line-width (e.g., 30 micrometers or more) on a substrate and methods of forming the same. A master tool is provided with an ink pattern on a major surface thereof. The ink pattern is formed by a screen printing process. A stamp-making material is applied to the major surface of the master tool to form a stamp having a stamping pattern being negative to the ink pattern of the master tool. A stamping surface of the stamping pattern is inked with an ink composition and contacted with a metalized surface to form a printed pattern on the metalized surface according to the stamping pattern. Using the printed pattern as an etching mask, the metalized surface is etched to form electrically conductive traces.

FIG. 1 is a flow diagram illustrating a method 100 of forming an electrically conductive pattern on a substrate, according to one embodiment. At 110, an ink pattern is screen-printed onto a major surface of a master tool. In some embodiments, the master tool can include, for example, a glass substrate. The ink pattern is formed by a screen printing process such as, for example, a method 200 shown in FIG. 2 which will be described further below. The method 100 then proceeds to 120.

At 120, a stamp is formed by applying a stamp-making material to the ink pattern on the major surface of the master tool. The stamp has a stamp pattern being negative to the ink pattern. In some embodiments, the stamp-making material can include one or more polymeric materials. In some embodiments, the stamp can be molded against the master tool by applying uncured polydimethylsiloxane (PDMS) to the master tool and then curing. The method 100 then proceeds to 130.

At 130, a stamping surface of the stamp pattern is inked with an ink composition. In some embodiments, the ink composition can include functionalizing molecules including a functional group selected to bind to a metalized surface. The method 100 then proceeds to 140.

At 140, the stamping surface is contacted with the metalized surface to create a printed pattern thereon. In some embodiments, the stamp is positioned and brought into contact with the metalized surface, and a pattern of the ink can be transferred from the stamping surface of the stamp to the metalized surface to form patterned self-assembled monolayers (SAMs) thereon. The method 100 then proceeds to 150.

At 150, electrically conductive traces are formed on the substrate by etching the metalized surface using the printed pattern as an etching mask. In some embodiments, the metalized surface can be an electrically conductive layer disposed on the substrate. The electrically conductive layer can be etched using the patterned SAMs as the etching mask. The exposed portion of the electrically conductive layer can be removed by etching and the remaining portion of the electrically conductive layer can be revealed as electrically conductive traces that form an electrically conductive pattern on the substrate.

Figure 2:
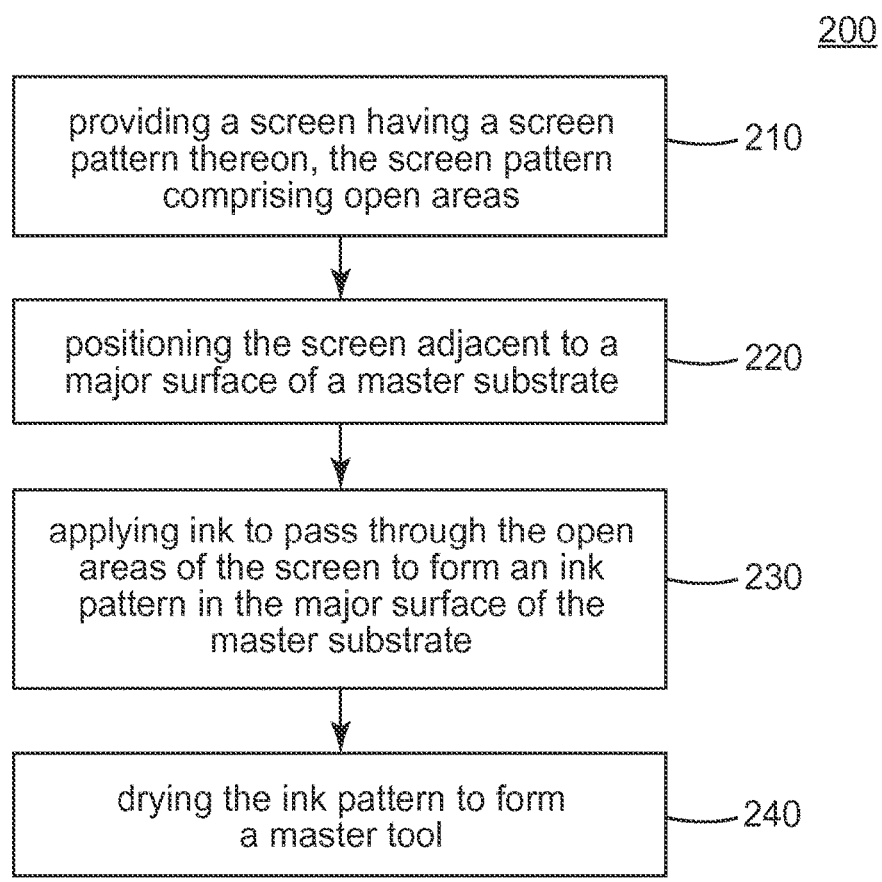
FIG. 2 is a flow diagram illustrating a method of forming a master tool having an ink pattern, according to one embodiment.

FIG. 2 is a flow diagram illustrating a method 200 of forming a master tool such as, for example, the master tool used in the method 100 of FIG. 1. At 210, a screen is provided with a screen pattern thereon. The screen pattern includes open areas that allow fluid to pass through the screen. In some embodiments, a photosensitive emulsion layer can be coated onto a mesh structure of a screen and the photosensitive emulsion layer can be exposed through a photomask to form a predetermined pattern. The unexposed areas of the photosensitive emulsion layer can be washed away to form the open areas. The method 200 then proceeds to 220.

At 220, the screen is positioned adjacent to a major surface of a master substrate. In some embodiments, the master substrate can be, for example, a glass substrate. The method 200 then proceeds to 230.

At 230, an ink is applied to pass through the open areas of the screen to form an ink pattern on the major surface of the master substrate. In some embodiments, the ink can be, for example, a ceramic high-temperature ink that can firmly adhere to the glass substrate after curing or drying. The method 200 then proceeds to 240.

At 240, the ink pattern is dried to form a master tool. In some embodiments, the ink pattern can include an arrangement of ink pattern elements extending away from the major surface of the master substrate, and one or more indentations formed between the respective adjacent ink pattern elements. In some embodiments, at least one of the indentations formed on the master tool has a lateral dimension of at least 30 micrometers, and a depth of at least 10 micrometers.

Figure 3:
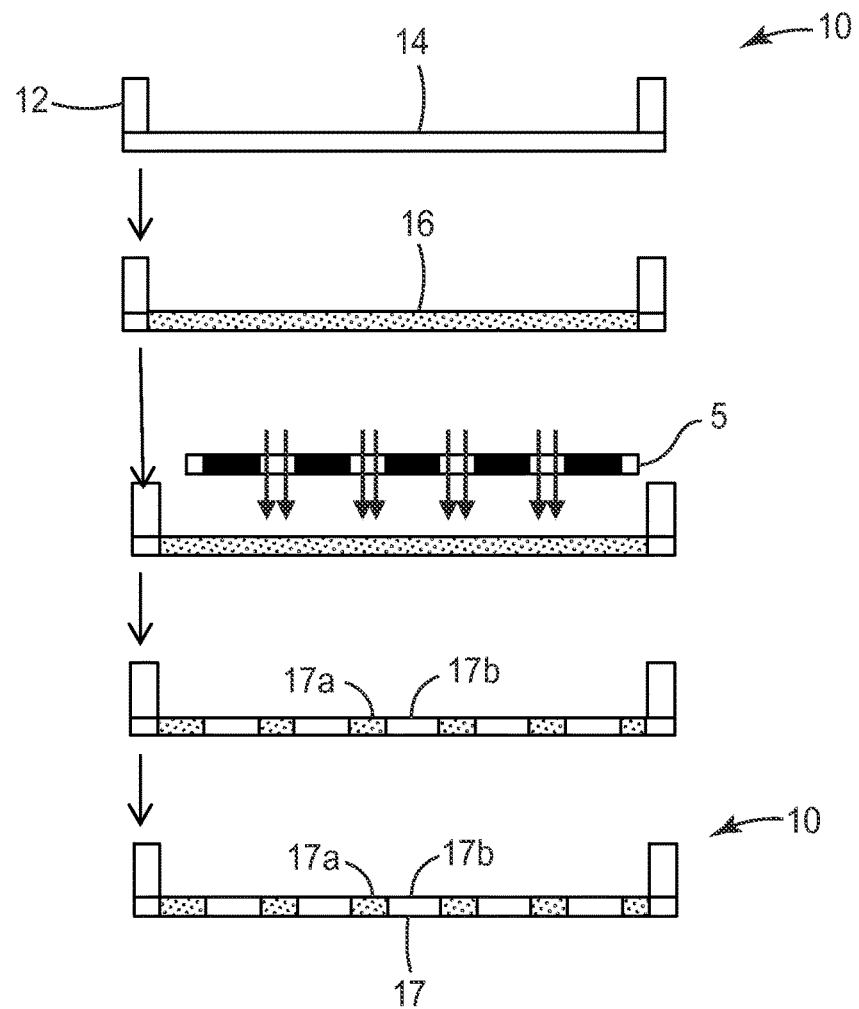
FIG. 3 is a schematic illustration of providing a screen having a screen pattern, according to one embodiment.

FIG. 3 is a schematic illustration of providing a screen having a screen pattern, according to one embodiment. A screen 10 includes a frame 12 and a mesh structure 14 mounted on the frame 12. In some embodiments, the mesh structure 14 can be woven from wires made from, for example, stainless steel. The mesh structure 14 can have a mesh number of, for example, 100 to 1000. An emulsion layer 16 is applied to the mesh structure 14. In some embodiments, the emulsion layer 16 can contain a photosensitive material including, for example, polyvinylacetate, poly vinyl alcohol, acrylate monomer, or a combination thereof. The thickness of the emulsion layer 16 can be, for example, 5 to 100 micrometers, 10 to 50 micrometers, or 15 to 30 micrometers. The emulsion layer 16 is exposed to, for example, a UV light, through a photomask 5, to form a predetermined pattern. Exposed areas 17a can be cured and unexposed areas can be washed away by a known cleaner to form open areas 17b. The cured areas 17a and the open areas 17b form a screen pattern 17. It is to be understood the screen 10 having the screen pattern 17 can be formed by any appropriate processes using appropriate materials.

FIG. 4 is a schematic illustration of forming a master tool 20, according to one embodiment. The screen 10 of FIG. 3 is positioned adjacent to a major surface 21 of a master substrate 22. The major surface 21 can have a surface roughness of, for example, less than 50 micrometers, less than 10 micrometers, less than 2 micrometers, less than 0.5 micrometers, or less than 0.1 micrometers. An ink 6 is applied to the screen 10 and a squeegee 7 is directed across the screen 10 at a predetermined angle, a predetermined speed, and a predetermined pressure, to squeeze the ink 6 to pass through the open areas 17b of the screen 10 to form an ink pattern 24 on the master substrate 22. In some embodiments, the ink 6 can be cured or dried on the master substrate 22 to form the ink pattern 24. In some embodiments, the major surface 21 of the master substrate 22 can be modified with chemicals to improve the bonding between the ink pattern 24 and the master substrate 22. In some embodiments, the master substrate 22 can be, for example, a glass substrate having a substantially planar surface, and the ink 6 can be, for example, a ceramic high-temperature ink that can firmly adhere to the glass substrate after curing or drying at a temperature of, for example, about 700° C. It is to be understood that any appropriate combination of materials for the master substrate 22 and the ink 6 can be used as long as the ink pattern 24 can be formed on the major surface 21 thereof.

The ink pattern 24 includes an arrangement of ink pattern elements 24a extending away from the major surface 21 and an arrangement of indentations 24b formed between the respective adjacent pattern elements 24a. The ink pattern elements 24a each can have a lateral dimension of, for example, at least 10 micrometers, at least 30 micrometers, at least 50 micrometers, between 30 micrometers and 1 mm, or between 50 and 800 micrometers. The ink pattern elements 24a each can have a relief height with respect to the major surface 21 of, for example, at least 5 micrometers, at least 10 micrometers, at least 20 micrometers, between 10 and 100 micrometers, or between 10 and 50 micrometers. In some embodiments, the ink pattern elements 24a can have a draft angle or side wall angle of, for example, 0 to 10 degrees, or 0.5 to 5 degrees with respect the major surface 21. The indentations 24b each have a bottom surface 26 that is an exposed portion of the major surface 21 of the master substrate 22. The indentations 24b each can have a lateral dimension of, for example, at least 10 micrometers, at least 30 micrometers, at least 50 micrometers, between 30 micrometers and 1 mm, or between 50 and 800 micrometers. The indentations 24b each can have a depth corresponding to the respective relief height of the ink pattern elements 24a. The depth of the indentations 24b can be, for example, at least 5 micrometers, at least 10 micrometers, at least 20 micrometers, between 10 and 100 micrometers, or between 10 and 50 micrometers.

The master tools described herein can provide an ink pattern thereon including an arrangement of ink pattern elements and indentations with a relatively wide lateral dimension (e.g., 30 micrometers or greater) and a relatively large relief height or depth (e.g., 10 micrometers or greater). Photoresist patterns on master tools prepared by conventional photolithography techniques generally have much narrower lateral dimensions (e.g., 10 micrometers or less) and much lower relief heights (e.g., 1 micrometer or less).

Figure 9:
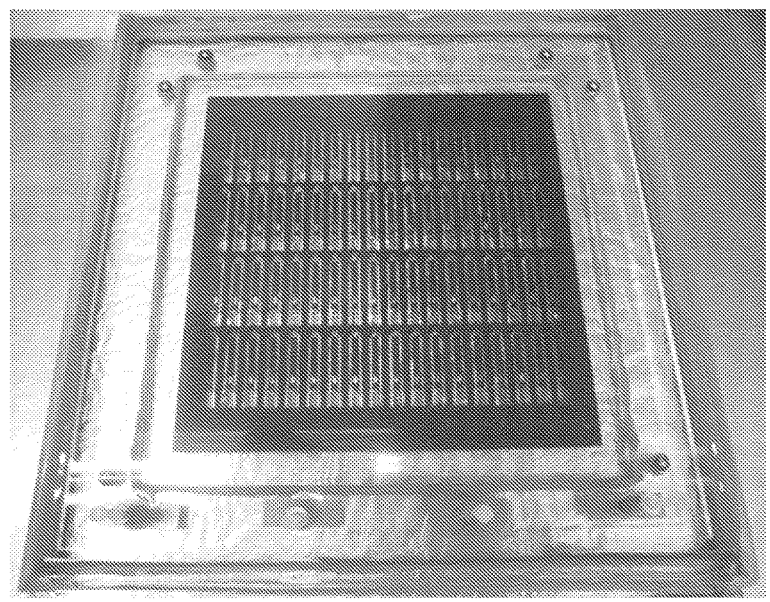
FIG. 9 is an image of a shallow tray for positioning the glass master and producing the PDMS stamp, according to Example 1.

FIG. 5 is a schematic illustration of forming a stamp 30, according to one embodiment. The master tool 20 of FIG. 4 can be placed, for example, inside a shallow tray as shown in FIG. 9. A layer of stamp-making material 32 is dispensed onto the ink pattern 24 to form a negative of the ink pattern 24. The layer of stamp-making material 32 can be hardened by curing to form the stamp 30. The stamp 30 includes a base surface 35 and an arrangement of pattern elements 36 extending away from the base surface 35. The base surface 35 can be substantially planar. In some embodiments, the stamp 30 can be a unitary block of an elastomeric material, and in other embodiments may include the pattern elements 36 supported by an optional reinforcing backing layer. The array of pattern elements 36 on the base surface 35 of the stamp 30 form a stamping pattern 34 that can vary widely depending on the intended microcontact printing application, and can include, for example, regular or irregular patterns of elements such as lines, dots, polygons, etc.

The stamp-making material 32 can include one or more polymeric materials including, for example, homopolymers, copolymers, etc. Polymeric materials suitable for use in fabrication of the stamp 30 may include, for example, silicones, polyurethanes, ethylene propylene diene M-class (EPDM) rubbers, as well as commercially available flexographic printing plate materials (for example, those commercially available from E. I. du Pont de Nemours and Company, Wilmington, Del., under the trade designation Cyrel). The stamp can be made from a composite material including, for example, an elastomeric material on the stamping surfaces 136 combined with a woven or non-woven fibrous reinforcement.

Polydimethylsiloxane (PDMS) is particularly useful as a stamp material, as it is elastomeric and has a low surface energy (which makes it easy to remove the stamp from most substrates). A useful commercially available formulation is available from Dow Corning, Midland, Mich., under the trade designation Sylgard 184 PDMS. PDMS stamps can be formed, for example, by dispensing an un-crosslinked PDMS polymer into or against a patterned mold such as, for example, the ink pattern 24, followed by curing. A master tool for molding the elastomeric stamps can be formed by the process as illustrated in FIG. 4 above. The elastomeric stamp can be molded against the master tool 20 by applying uncured PDMS to the master tool 20 and then curing.

The pattern elements 36 in the array on the base surface 35 can be described in terms of their shape, orientation, and size. The pattern elements 36 each include a stamping surface 136 that is formed according to the bottom surface 26 of the indentations 24b on the master tool 20 as shown in FIG. 4. The stamping surface 136 resides a height h above the base surface 35, and has a lateral dimension w. In some embodiments, the lateral dimension w can be, for example, at least 10 micrometers, at least 30 micrometers, at least 50 micrometers, between 30 micrometers and 1 mm, or between 50 and 800 micrometers. The height h can be, for example, at least 5 micrometers, at least 10 micrometers, at least 20 micrometers, between 10 and 100 micrometers, or between 20 and 50 micrometers. The spacing/between adjacent pattern elements 36 can be, for example, at least 10 micrometers, at least 30 micrometers, at least 50 micrometers, between 30 micrometers and 1 mm, or between 50 and 800 micrometers.

The pattern elements 36 can occupy all or just a portion of the base surface 35. In some embodiments, the array of pattern elements 36 for microcontact printing can cover areas of, for example, greater than 100 $cm^2$, greater than 400 $cm^2$, or greater than 1000 $cm^2$ on the base surface 35 of the stamp 30. In some embodiments, the pattern elements 36 can form a "micropattern", for example, the stamping pattern 34, which in this application, can refer to an arrangement of, for example, dots, lines, filled shapes, or a combination thereof. In some embodiments, the pattern elements 36 can include traces, which may be straight or curved, that can form a two-dimensional network (e.g., a mesh or a circuit).

Figure 6:
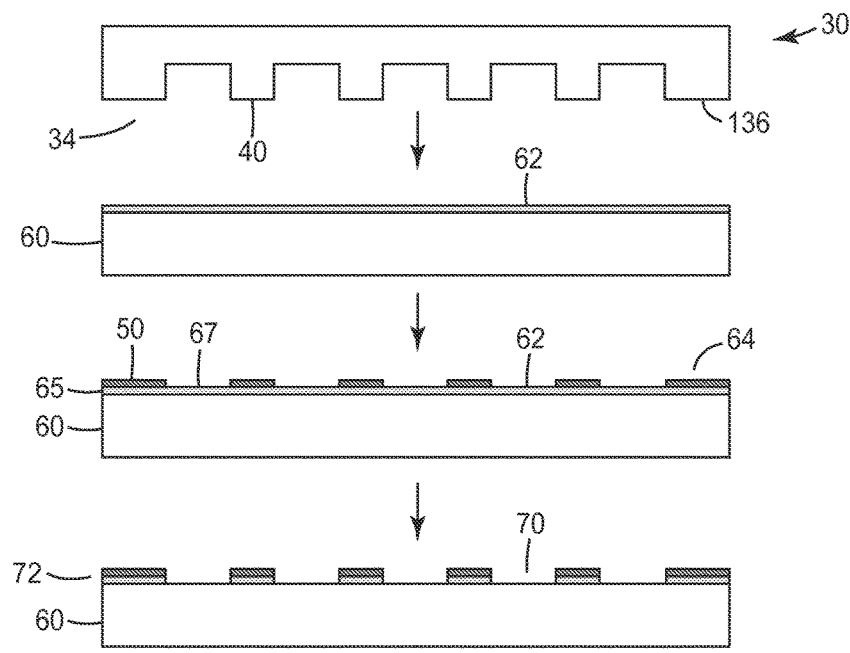
FIG. 6 is a schematic illustration of forming an electrically conductive pattern on a substrate, according to one embodiment.

FIG. 6 is a schematic illustration of forming an electrically conductive pattern on a substrate, according to one embodiment. An ink 40 including functionalizing molecules resides on the stamping surfaces 136 of the stamp 30. The functionalizing molecules in the ink 40 can include a functional group selected to bind to a material surface 62 on a substrate 60. The stamp 30 is positioned and is brought into contact with the material surface 62, and the stamping surfaces 136 are held against a first portion 65 of the material surface 62. The functionalizing molecules in the ink 40 are held against the material surface 62 to allow the functional group to bind thereto. Then, the stamping surfaces 136 are removed, and the ink remaining on the material surface 62 can chemically bind to the surface and forms a self-assembled monolayer (SAM) 50 on the first portions 65 of the material surface 62 according to the shapes and dimensions of the stamping surfaces 136. Portions 67 of the material surface 62, contiguous with first portions 65, remain free of the SAM 50. In this manner, a pattern of the ink 40 can be transferred from the stamping surface 136 on the stamp 30 to the material surface 62 of the substrate 60. The transferred pattern is illustrated as a printed pattern 64 that includes an arrangement of the SAMs 50 and corresponds to the stamping pattern 34 of the stamp 30.

In the embodiment of FIG. 6, the material surface 62 can be a metalized surface of the substrate 60. The material surface 62 can be formed by, for example, providing en electrically conductive layer onto the surface of the substrate 62. The electrically conductive layer 62 for supporting the SAMs 50 can include, for example, gold, silver, palladium, platinum, rhodium, copper, nickel, iron, indium, tin, tantalum, aluminum, as well as mixtures, alloys, and compounds of these elements. It is to be understood that the electrically conductive layer can include any suitable electrically conductive material. In one embodiment, the electrically conductive layer can include a composite material, for example, a metal-filled polymer. The electrically conductive layer on the substrate 60 can be any thickness such as, for example, from about 10 nanometers (nm) to about 100 micrometers. The electrically conductive layer can be deposited using any convenient method, for example sputtering, evaporation, chemical vapor deposition, or chemical solution deposition (including electroless plating).

In some embodiments, the material surface 62 can be a coating layer disposed on the substrate 60. Materials of the coating layer can include, for example, elemental metal, metal alloys, intermetallic compounds, metal oxides, metal sulfides, metal carbides, metal nitrides, and combinations thereof.

The material surface 62 and the ink 40 are selected such that the functionalizing molecules therein include a functional group that binds to the material surface 62 on the substrate 60. The functional group may reside at the physical terminus of a functionalizing molecule as well as any portion of a molecule available for forming a bond with the material surface 26 in a way that the molecular species can form the SAM 50, or any portion of a molecule that remains exposed when the molecule is involved in SAM formation. In some embodiments, the functionalizing molecules in the ink 40 may be thought of as having first and second terminal ends, separated by a spacer portion, the first terminal end including a functional group selected to bond to the material surface 62, and the second terminal group optionally including a functional group selected to provide the SAM 50 on the material surface 62 having a desirable exposed functionality. The spacer portion of the molecule may be selected to provide a particular thickness of the resultant SAM 50, as well as to facilitate the formation of the SAM 50. While the SAM 50 in the embodiments described herein may vary in thickness, the SAM 50 having a thickness of less than about 5 nanometers are generally preferred, more preferably those having a thickness of less than about 3 nanometers, and more preferably those having a thickness of less than about 1.5 nanometers. These dimensions are generally dictated by the selection of molecular species and in particular the spacer portion thereof.

In some embodiments, the SAM 50 formed on the material surface 62 on the substrate 60 may be modified after such formation for a variety of purposes. For example, a functionalizing molecule in the ink 40 may be deposited on the material surface 62 in the SAM 50, the functionalizing molecule having an exposed functionality including a protecting group which may be removed to effect further modification of the SAM 50. Alternately, a reactive group may be provided on an exposed portion of the functionalizing molecule in the ink 40 that may be activated or deactivated by electron beam lithography, x-ray lithography, or any other radiation. Such protections and de-protections may aid in chemical or physical modification of an existing surface-bound SAM 50.

In some embodiments, combinations of materials of the coating layer 62 and functional groups for functionalizing molecules in the ink 40 can include, for example: (1) metals such as gold, silver, copper, cadmium, zinc, palladium, platinum, mercury, lead, iron, chromium, manganese, tungsten, and any alloys of the above with sulfur-containing functional groups such as thiols, sulfides, disulfides, and the like; (2) doped or undoped silicon with silanes and chlorosilanes; (3) metal oxides such as silica, alumina, quartz, glass, and the like with carboxylic acids; (4) platinum and palladium with nitriles and isonitriles; and (4) copper with hydroxamic acids. Additional suitable functional groups on the functionalizing molecules in the ink 40 include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as the material for the material surface 62.

In some embodiments, the functionalizing molecules utilized to form the SAM 50 in the embodiments described herein are delivered to the stamp 30 as the ink 40 including one or more organosulfur compounds as described in U.S. Patent Application Pub. No. 2010/0258968. Each organosulfur compound is preferably a thiol compound capable of forming the SAM 50 on a selected portion 65 of the material surface 62. The thiols include the —SH functional group, and can also be called mercaptans. The thiol group is useful for creating a chemical bond between molecules of the functionalizing compound in the ink 40 and the material surface 62, for example, a metallic surface. Useful thiols can include, for example, alkyl thiols and aryl thiols. Other useful organosulfur compounds can include, for example, dialkyl disulfides, dialkyl sulfides, alkyl xanthates, dithiophosphates, and dialkylthiocarbamates.

In some embodiments, the ink 40 can include alkyl thiols such as, for example, linear alkyl thiols: $HS(CH_2)_nX$, wherein n is the number of methylene units and X is the end group of the alkyl chain (for example, X=—$CH_3$, —OH, —COOH, —$NH_2$, or the like). Preferably, X=—$CH_3$. Other useful functional groups include those described, for example, in: (1) Ulman, "Formation and Structure of Self-Assembled Monolayers", *Chemical Reviews* Vol. 96, pp. 1533-1554 (1996); and (2) Love et al., "Self-Assembled Monolayers of Thiolates on Metals as a Form of Nanotechnology", *Chemical Reviews* Vol. 105, pp. 1103-1169 (2005).

Useful alkyl thiols can be linear alkyl thiols (that is, straight chain alkyl thiols) or branched, and can be substituted or unsubstituted. The optional substituents preferably do not interfere with the formation of a SAM. Examples of branched alkyl thiols that are useful include alkyl thiols with a methyl group attached to every third or every fourth carbon atom of a linear alkyl chain backbone (for example, phytanylthiol). Examples of mid-chain substituents within useful alkyl thiols include ether groups and aromatic rings. Useful thiols can also include three-dimensional cyclic compounds (for example, 1-adamantanethiol). Preferred linear alkyl thiols have 10 to 20 carbon atoms (more preferably, 12 to 20 carbon atoms; most preferably 16 carbon atoms, 18 carbon atoms, or 20 carbon atoms).

Suitable alkyl thiols can include commercially available alkyl thiols (Aldrich Chemical Company, Milwaukee, Wis.). Preferably, the ink solutions 20 consist primarily of a solvent and the organosulfur compound, with impurities including less than about 5% by weight of the ink solution; more preferably less than about 1%; even more preferably less than about 0.1%. Useful inks 20 can contain mixtures of different organosulfur compounds dissolved in a common solvent such as, for example, mixtures of alkyl thiol and dialkyl disulfide.

Aryl thiols, which include a thiol group attached to an aromatic ring, are also useful in the ink 40. Examples of useful aryl thiols include biphenyl thiols and terphenyl thiols. The biphenyl and terphenyl thiols can be substituted with one or more functional groups at any of a variety of locations. Other examples of useful aryl thiols include acene thiols, which may or may not be substituted with functional groups. In some embodiments, useful thiols can include linear conjugated carbon-carbon bonds, for example double bonds or triple bonds, and can be partially or completely fluorinated.

The ink 40 can include two or more chemically distinct organosulfur compounds. For example, the ink can include two linear alkyl thiol compounds, each with a different chain length. As another example, the ink 40 can include two linear alkyl thiol compounds with different tail groups.

Although microcontact printing has been carried out using neat organosulfur compounds to ink the stamp, the delivery of organosulfur compounds to the stamp can be achieved more uniformly, and with less stamp swelling in the case of linear alkyl thiols and PDMS stamps, if delivered from a solvent-based ink. In some embodiments the ink 40 can include more than one solvent, but most useful formulations need include only a single solvent Inks formulated with only one solvent may contain small amounts of impurities or additives, for example stabilizers or desiccants.

Useful solvents are preferably compatible with PDMS (that is, they do not excessively swell PDMS), which is the most commonly used stamp material for microcontact printing. In microcontact printing, swelling of the PDMS stamp can lead to distortion of the patterned features and poor pattern fidelity. Depending on the inking approach, excessive swelling can also present significant challenges in providing mechanical support to the stamp.

Ketones can be suitable solvents for the ink solutions. In some embodiments, suitable solvents include, for example, acetone, methyl ethyl ketone, ethyl acetate, and the like, and combinations thereof. Acetone is a particularly preferred solvent. The one or more organosulfur compounds (for example, thiol compounds) are present in the solvent in a total concentration of at least about 3 millimoles (mM). As used herein, the "total concentration" refers to the molar concentration of all the dissolved organosulfur compounds taken in aggregate. The one or more organosulfur compounds (for example, thiol compounds) can be present in any total concentration in which the ink solution consists of essentially a single phase. The one or more organosulfur compounds (for example, thiol compounds) can be present in total concentrations of at least about 5 mM, at least about 10 mM, at least about 20 mM, at least 50 mM, and even at least about 100 mM.

The stamp 30 can be "inked" with the ink 40 of the embodiments described herein using methods known in the art (for example, as described in Libioulle et al. "Contact-Inking Stamps for Microcontact Printing of Alkanethiols on Gold", Langmuir Vol. 15, pp. 300-304 (1999)). In one approach, an applicator (for example, a cotton swab or a foam applicator) impregnated with the ink 40 can be rubbed across the stamping surfaces 136 of the stamp 30, followed by drying of solvent from the stamping surfaces 136. In another approach, the stamping surfaces 136 can be pressed against an "ink pad" impregnated with the ink solution, the ink pad optionally being a PDMS slab. In another approach, the stamp can be charged with ink solution from its back side, relative to the printing surface. In the latter approach, the organosulfur compound diffuses through the stamp 30 to reach the relief-patterned face for printing. In another embodiment, the relief-patterned printing face of the stamp 30 can be immersed in the ink solution, followed by withdrawal and drying ("immersive inking").

Referring again to FIG. 6, the material surface 62 (e.g., an electrically conductive layer) is etched using the SAMs 50 as an etching mask to remove the exposed portion 67. It is to be understood that the removal of the exposed portion 67 of the electrically conductive layer can be achieved through any appropriate process including, for example, dry etching, or wet chemical etching. After etching, electrically conductive traces 72 are formed on the substrate 60. The electrically conductive traces 72 correspond to the first portions 65 of the electrically conductive layer that are covered by the SAMs 50.

In some embodiments, at least one of the electrically conductive traces 72 has a lateral dimension of, for example, at least 10 micrometers, at least 30 micrometers, at least 50 micrometers, between 30 micrometers and 1 mm, or between 50 and 800 micrometers. The electrically conductive traces 72 on the substrate 60 can be any thickness such as, for example, from about 10 nanometers (nm) to about 100 micrometers. The electrically conductive traces 72 form an electrically conductive pattern 70 on the substrate 60. The remaining SAMs 50 can be washed away from the substrate 60 to reveal the electrically conductive pattern 70.

The substrate 60 can include, for example, a polymeric film, a glass, a silicon wafer, etc. In some embodiments, the substrate 60 can be a polymeric film that is in the form of a flat sheet and is sufficiently flexible and strong to be processed in a roll-to-roll fashion. Polymeric films used as substrates in articles described herein are sometimes referred to as base films. By roll-to-roll, what is meant is a process where material is wound onto or unwound from a support, as well as further processed in some way. Examples of further processes include coating, slitting, blanking, and exposing to radiation, or the like. Polymeric films can be manufactured in a variety of thicknesses, ranging in general from, for example, 5 micrometers to 1000 micrometers. In some embodiments, polymeric film thicknesses range from 25 micrometers to 500 micrometers, or from 50 micrometers to 250 micrometers, or from 75 micrometers to 200 micrometers. Roll-to-roll polymeric films may have a width of at least 12 inches, 24 inches, 36 inches, or 48 inches. Polymeric films can include, for example, poly(ethylene terephthalate) (PET), poly(butylenes terephthalate) (PBT), poly(ethylene naphthalate) (PEN), polycarbonate, cellulose triacetate, etc. In some embodiments, the substrate 60 can include PET, PBT, PEN, or a combination thereof.

In some embodiments, the substrate 60 can be flexible substrate where the flexible substrate material can be a polymeric film, a polymer material in the form of a flat sheet or web that is sufficiently flexible and strong to be processed in a roll-to-roll fashion. In some embodiments, the polymeric film web includes a relatively thin metal coating on a surface to which the ink from the stamp is to be applied. The metal coating may vary widely depending on the intended application, but should be sufficiently thin such that the web retains its flexibility as defined above.

Some embodiments described herein provide master tools that can be prepared by a screen printing process. Some master tools described herein, for example, the master tool 20 in FIG. 4, can provide pattern elements having a relief height of at least 10 micrometers, and a lateral dimension of at least 30 micrometers. The master tools can be used to form stamps such as, for example, the stamp 30 in FIG. 5 having one or more stamping pattern elements with a characteristic height of at least 10 micrometers and a lateral dimension of at least 30 micrometers. Some stamps provided herein can be used to create high-quality printed patterns on a substrate by microcontact printing. For example, since the stamping pattern elements are relatively high (e.g., 10 micrometers or more), possible edge blurring due to deformation of the stamping pattern elements can be effectively avoided. In contrast, it is technically difficult, time-consuming, and expensive to prepare photoresist patterns by conventional photolithography techniques (e.g., the photoresist pattern on silicon in U.S. Pat. No. 5,512,131) to obtain such high relief heights and such wide lateral dimensions as achieved in this disclosure. Using the photoresist patterns with relatively low relief heights (e.g., one micrometer or less), it would be technically challenging to produce, via microcontact printing, traces on a substrate with wide line-width (e.g., 30 micrometers or more) without blurring the edges of the traces.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

EXAMPLE

The Example(s) are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Example 1

Figure 7:
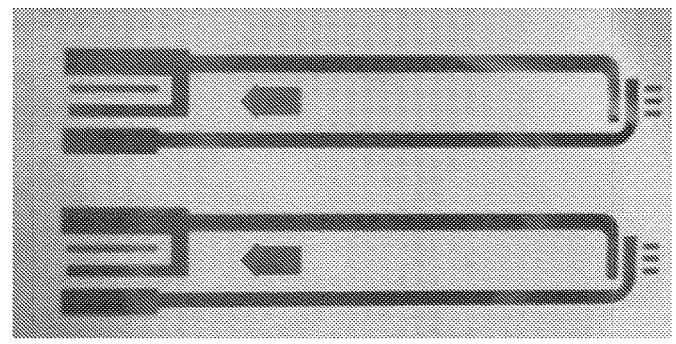
FIG. 7 is an image of an electrically conductive pattern with wide line-width on a transparent substrate, according to Example 1.

An exemplary PET film having a silver metal pattern on the surface thereof, as shown in FIG. 7, was made by the following processing steps:

(1) A screen is provided with a mesh structure woven from wires made from stainless steel. The mesh structure has a size of 65 cm×75 cm, and a mesh number of 400. A photosensitive emulsion with a thickness of about 20 micrometers was coated onto the mesh structure. The photosensitive emulsion is commercially available from Matina Co., Taiwan. The photosensitive emulsion was exposed to a UV light to produce pattern openings that consist of the areas to be printed. The pattern openings have a minimum line width of about 0.4 mm.

Figure 8:
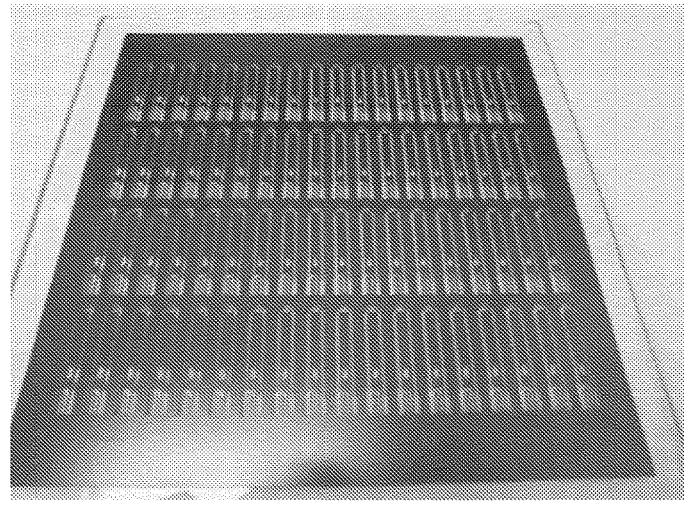
FIG. 8 is an image of a glass master of Example 1.

(2) A ceramic high-temperature ink is screen-printed, via the screen of step 1, onto a glass substrate to form a glass master having an ink pattern as shown in FIG. 8. The glass substrate has a size of 205 mm×195 mm and a thickness of 4.75 to 4.77 mm. The ink was dried at a temperature of about 700° C. The dried ink pattern has a thickness of about 10 to about 12 micrometers.

(3) The glass master was placed inside a shallow tray as shown in FIG. 9. A layer of uncured PDMS was dispensed onto the ink pattern of the glass master to form a negative of the ink pattern. The layer of uncured PDMS was hardened by curing to form a PDMS stamp.

(4) An inking material containing thiols was coated onto stamping surfaces of the PDMS stamp. The inking material contains 97% (dry weight) of 1-Hexadecanethiol and is commercially available from Alfa Aesar. A silver coated PET film (Dupont Melinex ST-504) was stamped by the PDMS stamp to form a pattern of SAMs on the silver coated PET film. The uncovered silver was etched by a chemical etchant to form silver traces on the PET film. The silver traces each have a minimum line width of about 0.4 mm. A portion of the electrically conductive pattern formed on the PET film was shown in FIG. 7. The electrically conductive pattern is used for a glucose test strip.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about."

Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:
1. A method comprising:
screen-printing an ink pattern onto a major surface of a master tool, the ink pattern comprising a plurality of ink pattern elements extending away from the major surface and one or more indentations formed between the respective ink pattern elements that are adjacent to each other, wherein screen-printing the ink pattern further comprises providing a screen which further comprises providing a photosensitive emulsion layer on a mesh structure of the screen, providing a photomask adjacent to the mesh structure, and exposing the photosensitive emulsion layer via the photomask to develop a screen pattern thereon; and
applying a stamp-making material to the major surface of the master tool to form an elastomeric stamp having a stamping pattern, the stamping pattern being negative to the ink pattern of the master tool, the stamping pattern comprising a base surface and one or more stamping pattern elements extending away from the base surface, the stamping pattern elements corresponding to the indentations of the master tool, and each of the stamping pattern elements having a stamping surface,
wherein at least one of the ink pattern elements has a relief height of at least 10 micrometers.

2. The method of claim 1, wherein at least one of the ink pattern elements has a lateral dimension of at least 30 micrometers.

3. The method of claim 1, wherein at least one of the ink pattern elements has a draft angle of 0 to 10 degrees.

4. The method of claim 1, wherein screen-printing the ink pattern further comprises positioning the screen adjacent to the major surface of the master tool, and applying ink to pass through the screen pattern to form an ink pattern on the major surface of the master tool.

5. The method of claim 1, wherein the photosensitive emulsion layer comprises a photosensitive material including polyvinylacetate, poly vinyl alcohol, acrylate monomer, or a combination thereof.

6. The method of claim 1, wherein the stamp-making material includes uncured polydimethylsiloxane (PDMS).

7. The method of claim 1, wherein the master tool comprises a glass substrate, and the ink pattern adheres to the glass substrate after curing or drying a ceramic high-temperature ink.

8. The method of claim 1, wherein at least one of the stamping surfaces has a lateral dimension of at least 30 micrometers.

9. The method of claim 1, wherein the screen pattern includes pattern openings having a minimum line width of about 100 micrometers.

10. A method of forming an electrically conductive pattern on a substrate, comprising:

providing a master tool having an ink pattern on a major surface of a master substrate thereof, the ink pattern comprising a plurality of ink pattern elements extending away from the major surface and one or more indentations formed between the respective ink pattern elements that are adjacent to each other, wherein the ink pattern is screen-printed onto the major surface of the master substrate, and at least one of the ink pattern elements has a relief height of at least 10 micrometers, and wherein screen-printing the ink pattern further comprises providing a screen which further comprises providing a photosensitive emulsion layer on a mesh structure of the screen, providing a photomask adjacent to the mesh structure, and exposing the photosensitive emulsion layer via the photomask to develop a screen pattern thereon;

applying a stamp-making material to the major surface of the master tool to form an elastomeric stamp having a stamping pattern, the stamping pattern being negative to the ink pattern of the master tool, the stamping pattern comprising a base surface and one or more stamping pattern elements extending away from the base surface, the stamping pattern elements corresponding to the indentations of the master tool, and each of the stamping pattern elements having a stamping surface;

inking the stamping surfaces of the stamp with an ink composition;

contacting the stamping surfaces of the stamp with a metalized surface of the substrate to transfer the ink composition from the stamping surfaces of the stamp to the metalized surface and create a printed pattern thereon; and etching, using the printed pattern as an etching mask, the metalized surface to form one or more electrically conductive traces on the substrate.

11. The method of claim 10, wherein providing the master tool further comprises providing a screen having a screen pattern with open areas thereon, applying ink to pass through the open areas of the screen to form the ink pattern on the major surface of a master substrate, and drying the ink pattern to form the master tool.

12. The method of claim 10, wherein at least one of the stamping pattern elements has a characteristic height of at least 10 micrometers.

13. The method of claim 10, wherein at least one of the stamping surfaces has a lateral dimension of at least 30 micrometers.

14. The method of claim 10, wherein the master tool comprises a glass substrate, and the ink pattern adheres to the glass substrate after curing or drying a ceramic high-temperature ink.

15. The method of claim 10, wherein the stamp-making material includes uncured polydimethylsiloxane (PDMS).

16. The method of claim 10, wherein the ink composition comprises a functionalizing molecule, wherein the functionalizing molecule comprises a functional group capable of binding to the metalized surface of the substrate.

17. The method of claim 10, wherein the substrate includes a polymeric film and a metal layer disposed on the polymeric film.

18. The method of claim 17, wherein the polymeric film comprises poly(ethylene terephthalate) (PET), poly(butylenes terephthalate) (PBT), poly(ethylerne naphthalate) (PEN), or a combination thereof.

19. The method of claim 17, wherein the metal layer includes at least one of copper, silver, aluminum, gold, and combinations thereof.

* * * * *